(12) United States Patent
Yoon et al.

(10) Patent No.: US 8,025,872 B2
(45) Date of Patent: Sep. 27, 2011

(54) OSTEOGENIC SYNTHETIC PEPTIDES, PHARMACEUTICAL COMPOSITIONS COMPRISING THE SAME, AND MEDIUM CONTAINING THE SAME

(75) Inventors: Taek Rim Yoon, Gwangju (KR); Hyung Keun Kim, Jeollanam-Do (KR); Ji Hyun Kim, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 222 days.

(21) Appl. No.: 12/453,584

(22) Filed: May 15, 2009

(65) Prior Publication Data

US 2010/0016236 A1 Jan. 21, 2010

(30) Foreign Application Priority Data

May 16, 2008 (KR) .................. 10-2008-0045461
Jun. 20, 2008 (KR) .................. 10-2008-0058551

(51) Int. Cl.
*A61K 38/04* (2006.01)
*C07K 7/08* (2006.01)

(52) U.S. Cl. ............................ 424/84; 514/1.1; 530/326
(58) Field of Classification Search ........................ None
See application file for complete search history.

(56) References Cited

U.S. PATENT DOCUMENTS

2006/0122109 A1 6/2006 Cho et al.

FOREIGN PATENT DOCUMENTS

| WO | WO 90/11366 A1 | 10/1990 |
| WO | WO 2006/072623 A1 | 7/2006 |
| WO | WO 2009/139525 A1 | 11/2009 |
| WO | WO 2009/154330 A1 | 12/2009 |
| WO | 2010037395 A2 | 4/2010 |

OTHER PUBLICATIONS

Tingting Li et al. "Bone morphogenetic protein 7: a novel treatment for chronic renal and bone disease" Current Opinion in Nephrology and Hypertension, Jul. 1, 2004, vol. 13, No. 4, pp. 417-422, XP002565669. Abstract.
Li T., et al., "Bone morphogenetic protein 7: a novel treatment for chronic renal and bone disease", Curr Opin Nephrol Hypertens, vol. 13(4), pp. 417-422, (Jul. 2004).
Swencki-Underwood, B., et al., "Expression and characterization of a human BMP-7 variant with improved biochemical properties", Protein Expression and Purification, vol. 57(2), pp. 312-319, (2008).
Greenwald, J., et al., "The BMP7/ActRII Extracellular Domain Complex Provides New Insights into the Cooperative Nature of Receptor Assembly", Molecular Cell, vol. 11(3), pp. 605-617, (Mar. 2003).
Communication and Supplementary European Search Report issued on May 3, 2011, in corresponding European Application No. 08874286.1, five (5) pages.
Özkaynak, Engin, et al., "OP-1 cDNA encodes an osteogenic protein in the TGF-β family," The EMBO Journal, 1990, pp. 2085-2093, vol. 9, No. 7, Oxford University Press.
Li, Tingting et al., "Bone Morphogenetic Protein 7: A Novel Treatment for Chronic Renal and Bone Disease," Current Opinion in Nephrology and Hypertension, 2004, pp. 417-422, vol. 13, No. 4, Lippincott Williams & Wilkins.
Extended Search Report issued on Jun. 20, 2011, in corresponding European Application No. 08874714.2, four (4) pages.

*Primary Examiner* — Prema Mertz
(74) *Attorney, Agent, or Firm* — The Nath Law Group; Joshua B. Goldberg; Mihsuhn Koh

(57) ABSTRACT

Disclosed herein is an osteogenic synthetic peptide, derived from bone morphogenetic protein-7, consisting of a sequence of 15 amino acid residues. Provided are also a pharmaceutical composition and a medium composition comprising the same. Having remarkable activity related to promoting osteoblast differentiation, the osteogenic synthetic peptide is very useful in the treatment of osteoporosis, bone defects and/or osteoarthritis.

3 Claims, 19 Drawing Sheets

FIG. 1a
Gly-Gln-Gly-Phe-Ser-Tyr-Pro-Tyr-Lys-Ala-Val-Phe-Ser-Thr-Gln
(G-Q-G-F-S-Y-P-Y-K-A-V-F-S-T-Q)
FIG. 1b
Val-Glu-His-Asp-Lys-Glu-Phe-Phe-His-Pro-Arg-Tyr-His-His-Arg
(V-E-H-D-K-E-F-F-H-P-R-Y-H-H-R)
FIG. 2a
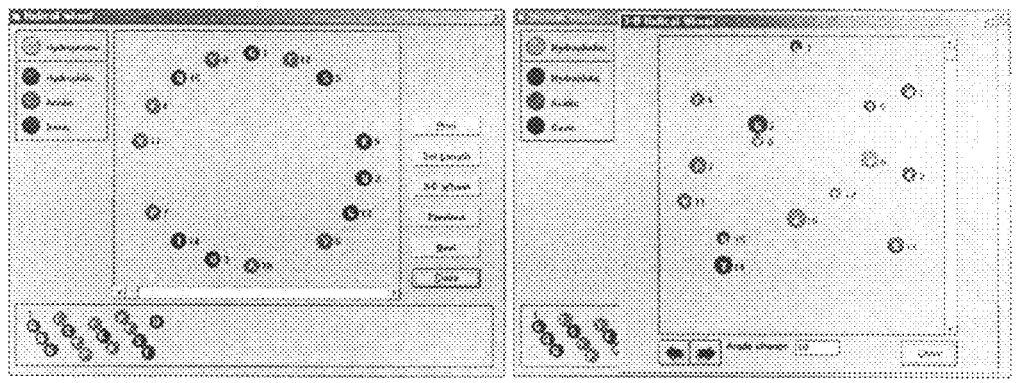
FIG. 2b
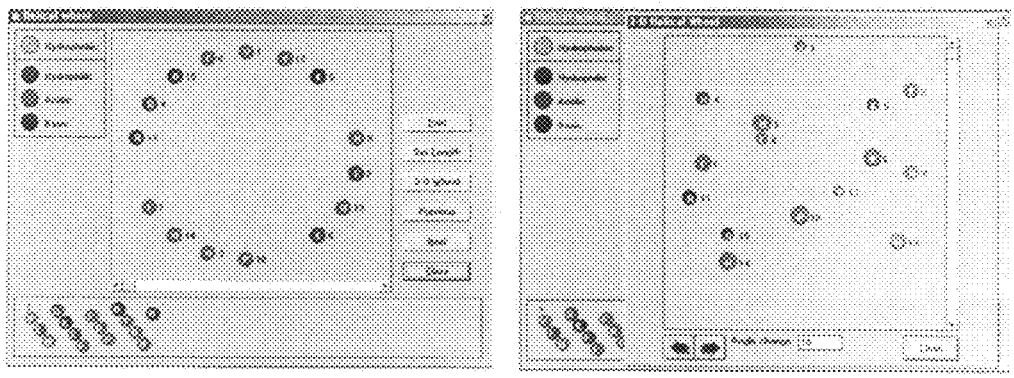

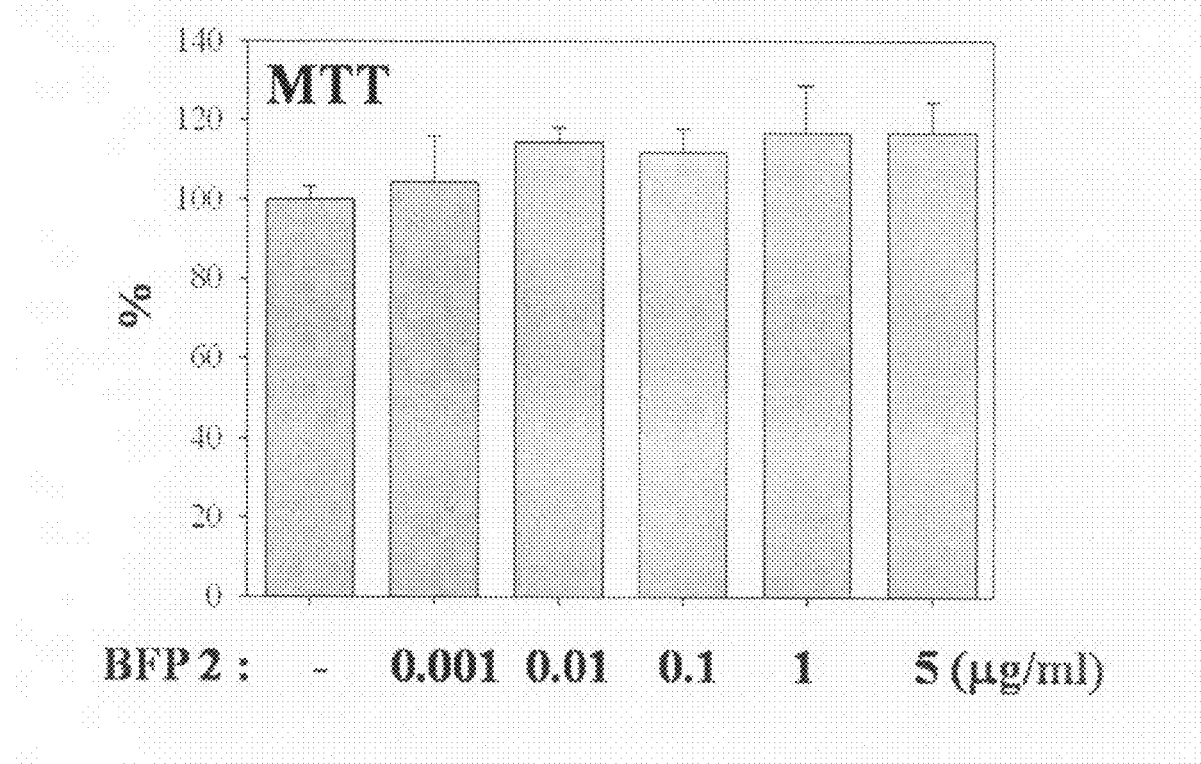

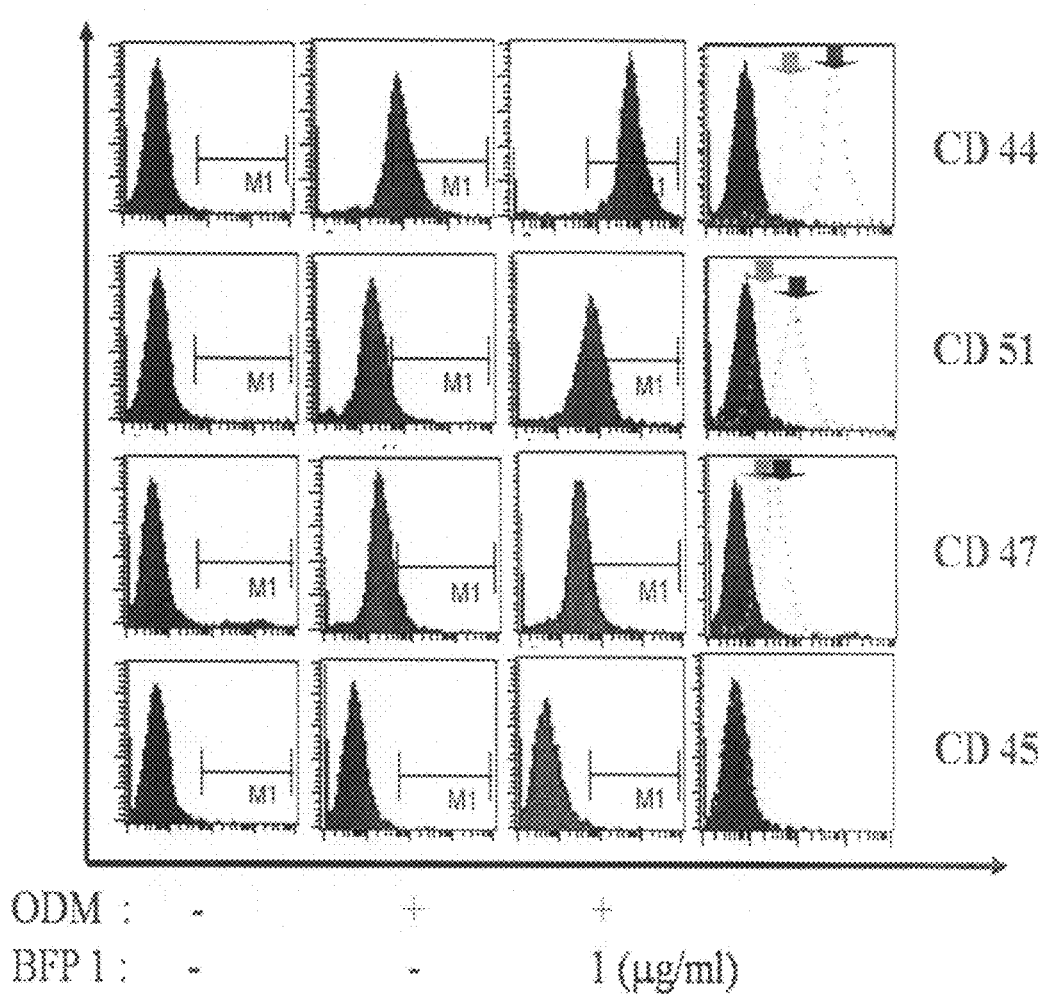

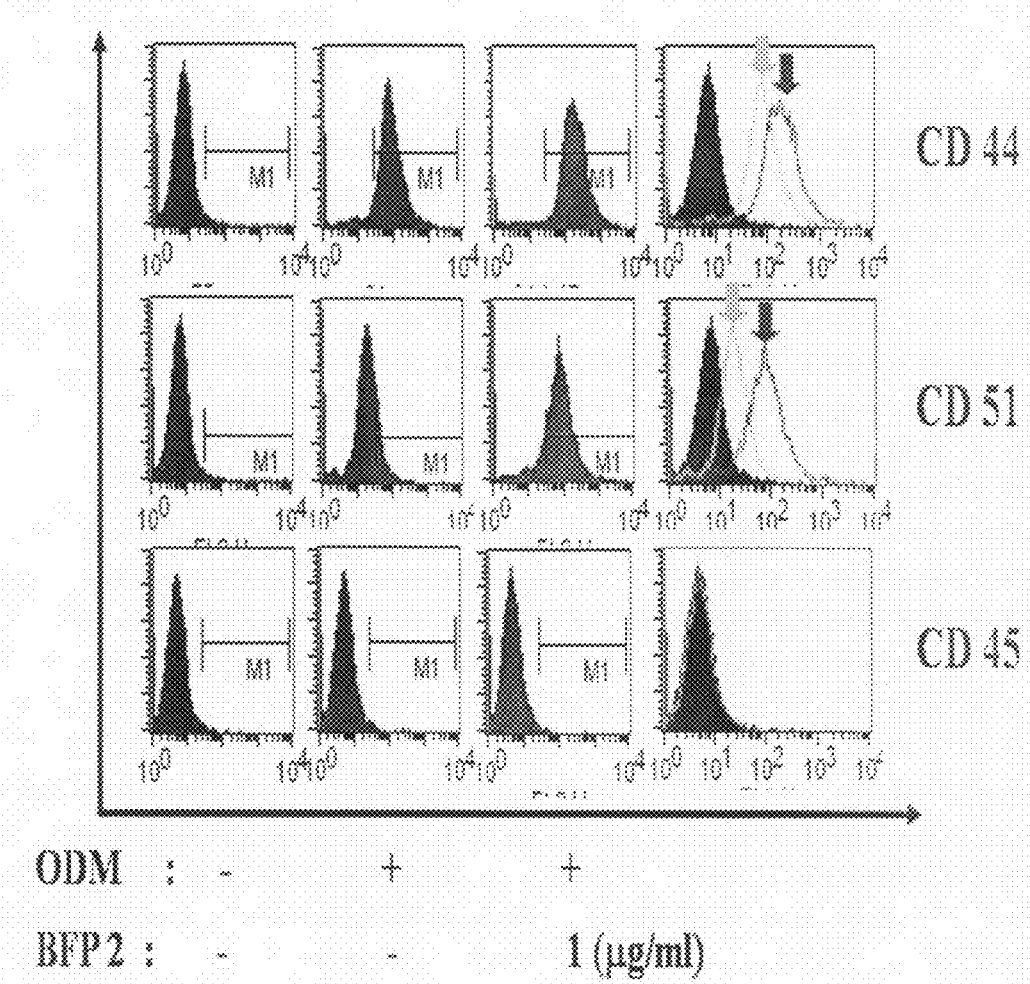

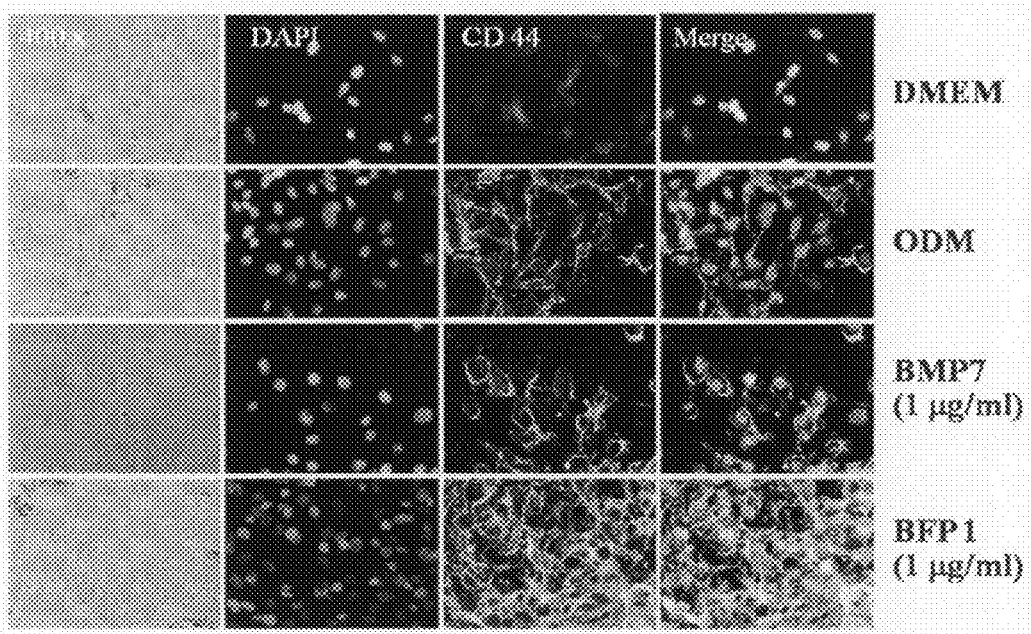
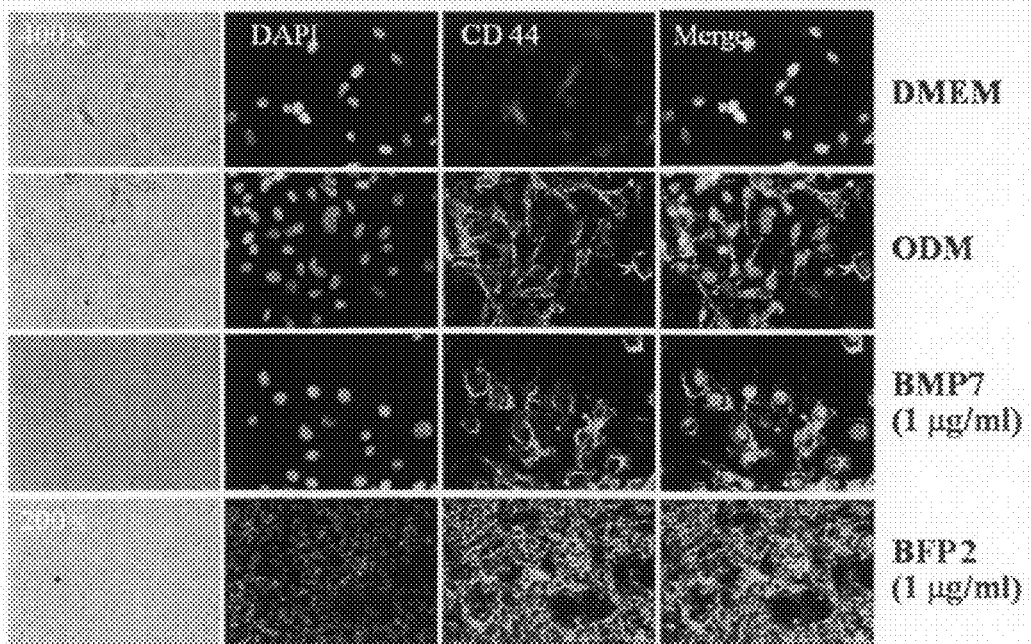

FIG. 11a
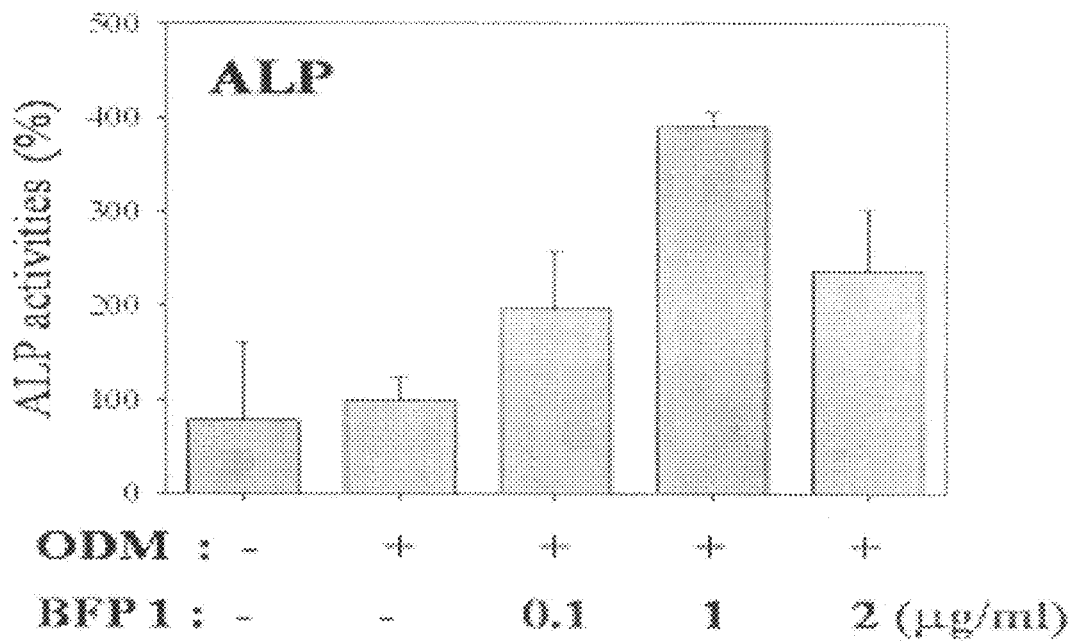
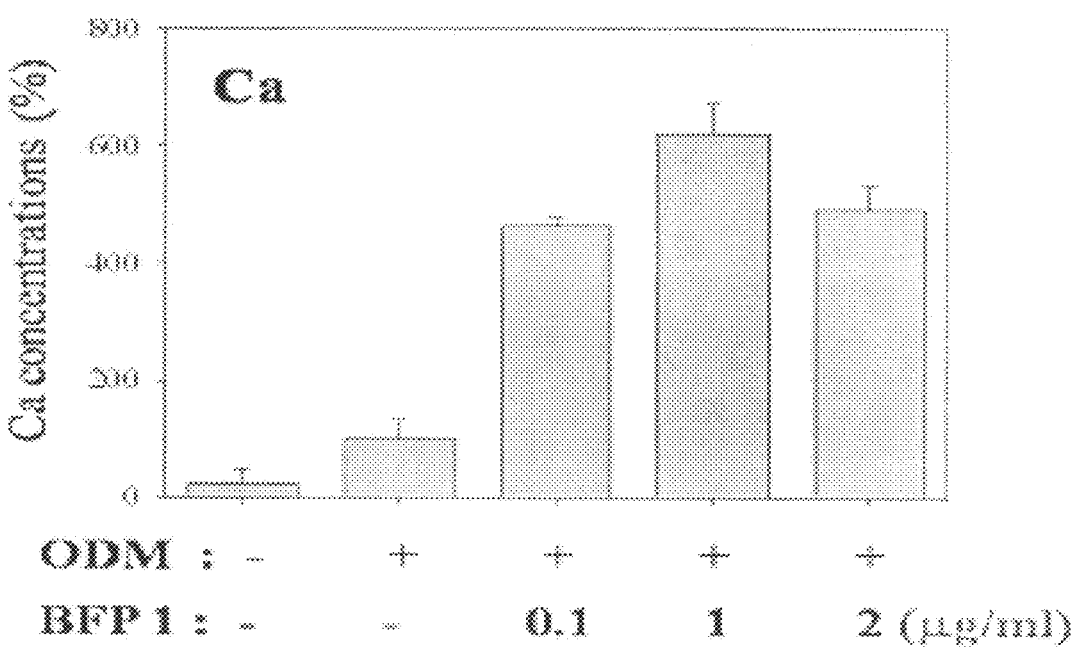

FIG. 14a
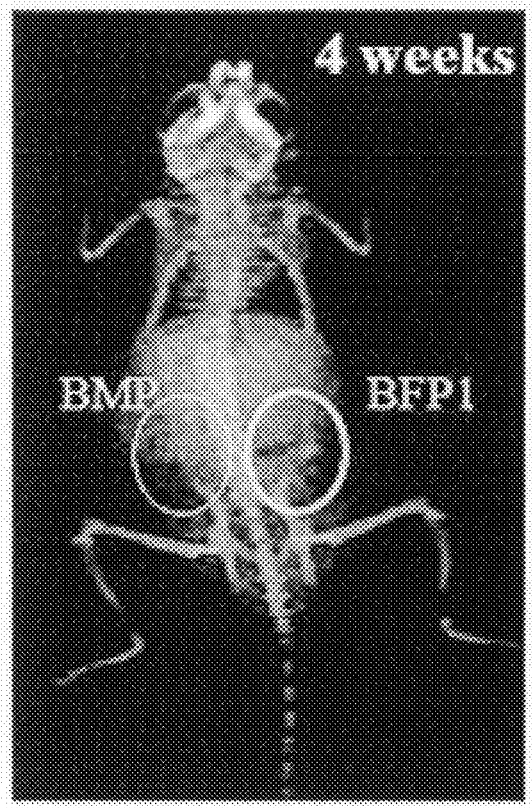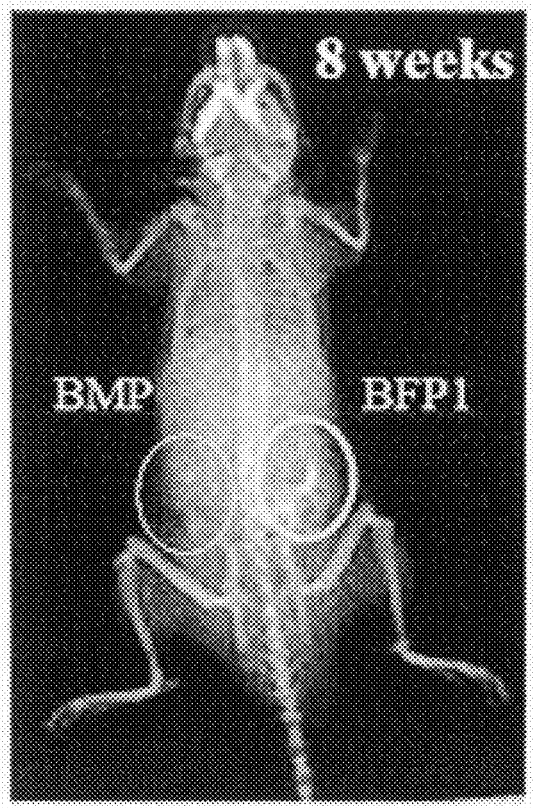

FIG. 14b
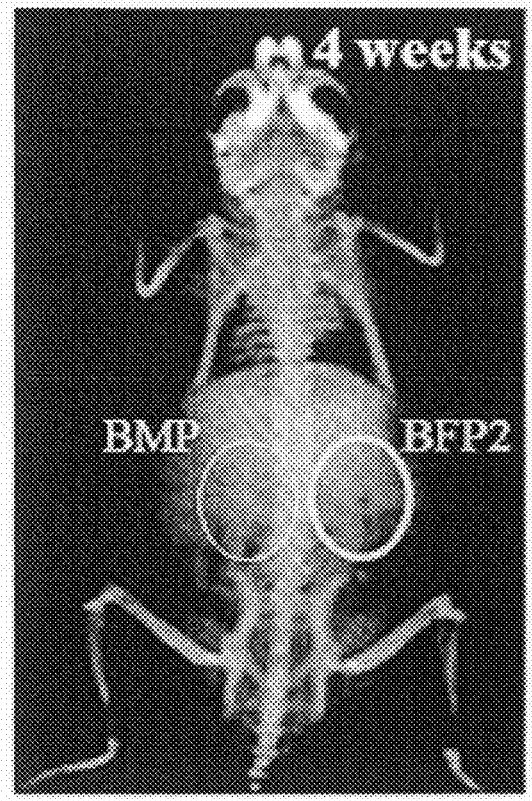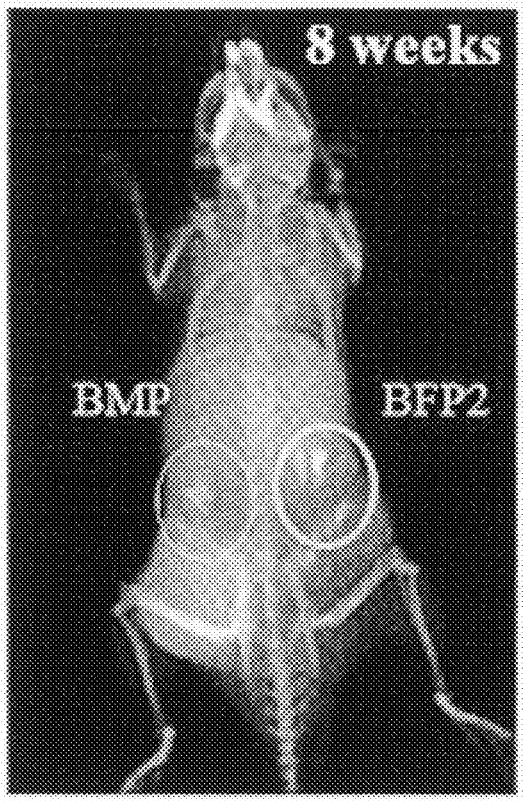

BMP

BFP 1

BMP

BFP 2

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Bone forming peptide 1(BFP1) is derived from
      BMP-7

<400> SEQUENCE: 1

Gly Gln Gly Phe Ser Tyr Pro Tyr Lys Ala Val Phe Ser Thr Gln
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Bone forming peptide 2(BFP2) is derived from
      BMP-7

<400> SEQUENCE: 2

Val Glu His Asp Lys Glu Phe Phe His Pro Arg Tyr His His Arg
1               5                   10                  15
```

US 8,025,872 B2

OSTEOGENIC SYNTHETIC PEPTIDES, PHARMACEUTICAL COMPOSITIONS COMPRISING THE SAME, AND MEDIUM CONTAINING THE SAME

BACKGROUND OF THE INVENTION

1. Field of the Invention

The present invention relates generally to a peptide with an effective function and, more particularly, to a synthetic peptide, derived from BMP-7 (bone morphogenetic protein-7) and consisting of 15 amino acids, and a pharmaceutical composition and a medium composition comprising the same.

2. Description of the Related Art

Osteoporosis is a disease of bone that leads to an increased risk of fracture because the bone mineral density (BMD) is reduced, bone micro architecture is disrupted and the medullary cavity is enlarged.

The bone mass, accounting for the state of health of the bone, is dependent on various factors, such as heredity, nutrition, hormonal changes, exercise, life style, etc. Particularly, aging, shortage of exercise, low body weight, smoking, a low-calcium diet, menopause, or ovary resection are known to be causes of osteoporosis.

Because of the lower bone resorption level thereof, black people are generally higher in bone mass than are white people although there are differences between individuals. On the whole, the bone mass peaks at fourteen to eighteen years of age, and decreases by 1% per year in old age. Particularly, women over 30 years old continuously decrease in bone mass. Hormonal change at menopause causes the bone mass to rapidly decrease. In detail, women in menopause experience a rapid decrease of estrogen, which allows the production of an increased level of B-lymphocytes and the accumulation of pre-B cells in the bone marrow, causing an increase in IL-6 level. IL-6 acts to activate osteoclasts, thus decreasing the bone marrow.

Osteoporosis, as described above, inevitably accompanies senescence, especially post-menopausal women. Entering senescent societies, advanced countries have increasingly paid attention to osteoporosis and therapy therefor.

In addition to osteoporosis, osteoarthritis and bone defective disease are representative bone diseases. Osteoarthritis is known as degenerative arthritis entailing local degradation of joints including articular cartilage and the subchondral bone next to it. Osteoarthritis has two typical causes: when an excessive load is imposed to the joint although articular cartilage or the subchondral bone is normal; and when articular cartilage or the subchondral bone is weak, and even though a proper load is imposed to the joint.

Bone defects may be found in many sites of the body. Its main causes include acute trauma with the accompaniment of ossein loss, a tissue resection operation accompanied by bone loss, chronic inflammation with the accompaniment of bone resection, and chronic nonunion with the accompaniment of the segmental bone defects.

As concerns the medicine for bone diseases, the world market therefor amounts to about one hundred thirty billion dollars and is expected to gradually expand. Thus, leading research institutes and pharmaceutical companies have invested a lot of money in developing therapeutics for bone diseases.

For example, currently used therapeutics for osteoporosis include estrogen, androgenic anabolic steroids, calcium agents, phosphates, fluorine agents, Ipriflavone, and vitamin D3. Additional examples include aminobisphophonate, developed by Merck in 1995, and raloxifene, acting as a selective estrogen receptor modulator (SERM), developed by Lilly Co. in 1997.

Acting as a negative regulator of bone resorption, estrogen is now most widely used as a therapeutic for osteoporosis, but the habitual use thereof may increase the incidence of endometrial cancer and breast cancer and cause thrombosis, gallstones, hypertension, edema, and mastodynia. A group of studies shows that menopausal women co-administered with estrogen and progesterone are highly apt to suffer from breast cancer, stroke, and pulmonary embolism.

Turning to other therapeutics for osteoporosis, there are bisphosophonate agents (alendronate, etidronate), vitamin D agents, calcitonin agents, and calcium agents. However, bisphosphonate agents cause esophagitis in addition to being low in adsorptivity and difficult to take.

Vitamin D agents are expensive and have pharmaceutical effects which are still unknown. Calcitonin agents are expensive and difficult to take. Calcium agents, although with low side effects, are preventive of rather than therapeutic for osteoporosis.

Further, osteoporosis cannot be cured in the short term, but requires long-term administration of drugs. Accordingly, there is a need for a novel material which shows none of the above-mentioned side effects and is therapeutically effective enough to replace conventional drugs.

Furthermore, the prophylaxis and treatment of osteoporosis still remains to be improved. Particularly, the secondary osteoporosis resulting from drug abuse becomes aggravated.

Such situations are true of osteoarthritis and bone defects.

SUMMARY OF THE INVENTION

Leading to the present invention, intensive and thorough research into therapeutics for osteoporosis, conducted by the present inventors, aiming to overcome the problems encountered in the prior art, resulted in the finding that a peptide derived from BMP-7 is promotive of osteoblast differentiation.

It is therefore an object of the present invention to provide a synthetic peptide, derived from BMP-7, consisting of 15 amino acid residues, which promotes osteoblast differentiation or osteogenesis and can be synthesized at a low cost.

It is another object of the present invention to provide a pharmaceutical composition comprising the osteogenic synthetic peptide as an active ingredient, which is effective for the treatment of osteoporosis, osteoarthritis and/or bone defects, without side effects and producible at low cost.

It is a further object of the present invention to provide a medium composition for osteoblast differentiation, comprising the osteogenic synthetic peptide, with which the rate of osteoblast differentiation or bone formation can be controlled according to the intention of the user.

It should be noted that the objects of the present invention are not limited to the above-mentioned objects, and other non-mentioned objects can be clearly understood to those skilled in the art from the following description.

In order to accomplish the above objects, the present invention provides an osteogenic synthetic peptide, having a BMP-7-derived sequence of 15 amino acid resides, for promoting osteoblast differentiation or bone formation.

In a preferred modification, the osteogenic synthetic peptide has an amino sequence of SEQ ID NO. 1 or an analog thereof:

SEQ ID NO. 1:
Gly-Gln-Gly-Phe-Ser-Tyr-Pro-Tyr-Lys-Ala-Val-Phe-Ser-Thr-Gln

In another preferred modification, the osteogenic synthetic peptide has an amino sequence of SEQ ID NO. 1 or an analog thereof:

SEQ ID NO. 2:
Val-Glu-His-Asp-Lys-Glu-Phe-Phe-His-Pro-Arg-Tyr-His-His-Arg

In a preferred embodiment, an effective dose of the synthetic peptide for promoting osteoblast differentiation or bone formation is from 0.1 to 2 μg/ml.

In addition, the present invention provides a pharmaceutical composition comprising the osteogenic synthetic peptide of one of claims 1 to 4 or a non-toxic salt thereof alone or in combination with a pharmaceutically or veterinarilly acceptable liquid or solid vehicle.

In a preferred embodiment, the synthetic peptide or the non-toxic salt thereof is used as an active ingredient for treatment of osteoporosis, osteoarthritis and bone defects.

Also, the present invention provides an osteogenic differentiation medium, comprising the osteogenic synthetic peptide of one of claims 1 to 4 or a non-toxic salt thereof, in combination with a liquid or solid ingredient acceptable for medium preparation.

BRIEF DESCRIPTION OF THE DRAWINGS

The above and other objects, features and advantages of the present invention will be more clearly understood from the following detailed description taken in conjunction with the accompanying drawings, in which:

FIGS. 1a and 1b respectively show amino acid sequences of BFP 1 and BFP 2, the osteogenic synthetic peptides of the present invention;

FIGS. 2a and 2b are photographs taken of monitor screens on which structures of BFP 1 and BFP 2 are displayed;

FIGS. 9a and 9b show FACS cytometry analysis of the expression of cell surface markers accounting for osteoblast differentiation in the presence of BFP 1 and BFP 2, respectively (grey arrows—ODM alone; black arrows—ODM+ synthetic peptide);

FIGS. 10a and 10b are fluorescence microphotographs showing the expression of the cell surface marker CD44 in the presence of BFP1 and BFP 2, respectively;

FIGS. 11a and 11b are histograms showing the effects of BFP 1 and BFP 2 on the expression of the osteoblast-specific alkaline phosphatase (ALP) and calcium deposit as determined by a commercially available kit;

FIGS. 14a and 14b are X-ray photographs of mice implanted with BFP 1 or BFP 2-treated osteoblasts, showing the effect of BFP 1 and BFP 2 on bone formation.

DESCRIPTION OF THE PREFERRED EMBODIMENTS

Figure 3:
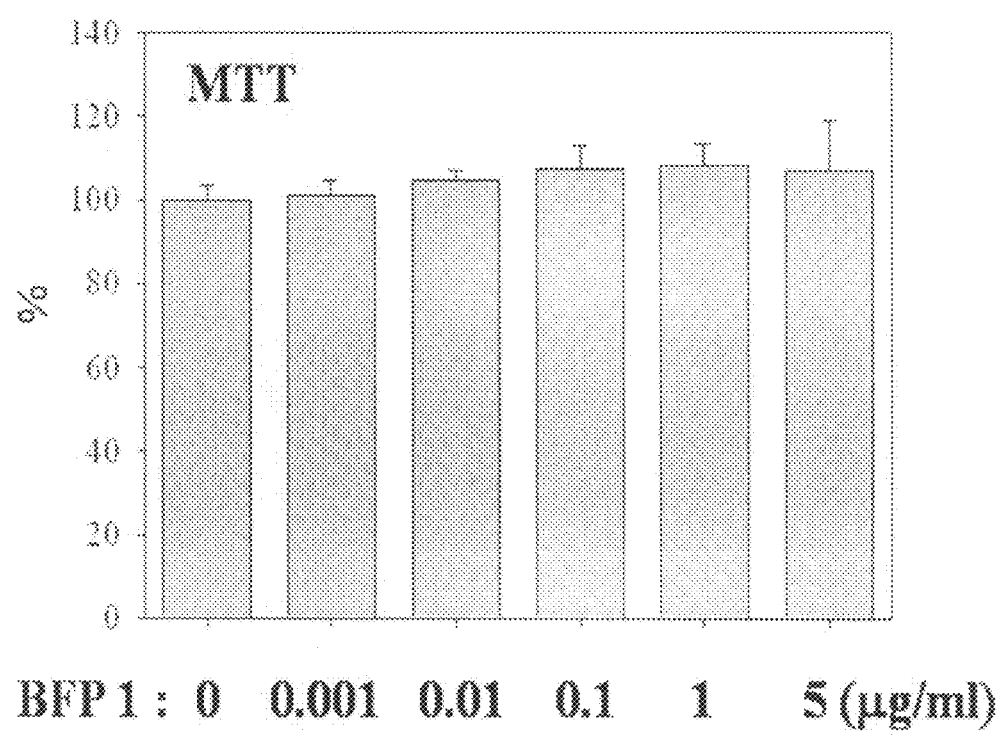
FIGS. 3a and 3b are histograms showing the cytotoxicity of BFP 1 and BFP 2.

The terminology used in the present invention is taken from the most widely used general terms, but in particular cases, it may come from the thesaurus of the present inventors. It should be noted that the meanings of the terms used in the specification and the following claims must be understood in consideration of the detailed description of the present invention or in association with the total context of the specification, and are not to be understood without reference thereto.

Below, a detailed description will be given of the structural constitution of the present invention, with reference to the following drawings.

As concerns bone morphogenetic activity, it was found that bone morphogenetic proteins (BMPs) which belong to the TGF-β (transforming growth factor-β) super family of proteins (Science 150, 893-897, 1965; Science 242; 1528-1534, 1988) are responsible for it. Well known are fourteen BMPs named BMP-1 to BMP-14. Of them, BMP-2 to BMP-14 are known to have bone morphogenetic activity. Although considered effective for the treatment of various bone dysfunctions and bone diseases, BMP-2 to BMP-14 are present in trace amounts in nature. Thus, the production of a large amount of BMP-2 to BMP-14 has to make recourse to a recombinant technique. In general, the production of recombinant proteins is expensive as compared to low-molecular weight compounds. In addition, the proteinous characteristics thereof bring about many limitations to the use of BMPs as drugs in terms of properties and administration. In consideration of these situations, a low-molecular weight organic compound having activity identical to that of BMP, if present, may be a promising drug.

As a result of intensive study into the amino acid sequences of BMP-7, the present inventors found that the following two amino acid sequences derived from BMP-7, each consisting of 15 amino acid residues, induce the expression of human BMP-7 in addition to having activity identical to that of human BMP-7. They were named bone forming peptide 1 (BFP 1) and bone forming peptide 2 (BFP 2), respectively.

SEQ ID NO. 1:
Gly-Gln-Gly-Phe-Ser-Tyr-Pro-Tyr-Lys-Ala-Val-Phe-
Ser-Thr-Gln

SEQ ID NO. 2:
Val-Glu-His-Asp-Lys-Glu-Phe-Phe-His-Pro-Arg-Tyr-
His-His-Arg

Although derived from BMP-7, BFP 1 and BFP 2, each consisting of 15 amino acid residues, can be synthesized using a known peptide synthesis method.

As will be clearly elucidated in the following experimental examples, osteoblasts (more accurately, mouse bone marrow stromal cells) are more intensively induced into differentiation when in the presence of BFP 1 or BFP 2.

Hence, the synthetic peptides for promoting osteogenesis, each having a BMP-7-derived amino acid sequence of 15 amino acid residues, that is, BFP 1 and BFP 2, enhance the differentiation of osteoblasts into mature bone cells, thus showing osteogenesis promoting activity.

From the fact that the synthetic peptides promoting osteogenesis in accordance with the present invention have excellent activity related to inducing the differentiation of osteoblasts, it can be inferred that when bone loss is caused by a bone disease such as osteoporosis, osteoarthritis or a bone defect, a pharmaceutical composition comprising as an active ingredient the synthetic peptide of the present invention or a non-toxic salt thereof may be applied to the site of bone loss so as to treat osteoporosis, osteoarthritis and/or the bone defect.

With reference to the accompanying drawings, an explanation is given of the activity of the osteogenesis-promoting synthetic peptides derived from BMP-7 in accordance with the present invention, BFP 1 and BFP 2, to induce osteoblast differentiation and bone formation.

FIG. 1 to FIG. 3 show amino acid sequences, structures and cytotoxicity of BFP 1 and BFP 2, respectively.

BFP 1 and BFP 2 shown in FIGS. 1a and 1b are identical to partial amino acid sequences of BMP-7 and can be synthesized to have 15-mer peptide sequences of SEQ ID NOS. 1 and 2, respectively.

SEQ ID NO. 1:
Gly-Gln-Gly-Phe-Ser-Tyr-Pro-Tyr-Lys-Ala-Val-Phe-
Ser-Thr-Gln
(G-Q-G-F-S-Y-P-Y-K-A-V-F-S-T-Q)

SEQ ID NO. 2:
Val-Glu-His-Asp-Lys-Glu-Phe-Phe-His-Pro-Arg-Tyr-
His-His-Arg
(V-E-H-D-K-E-F-F-H-P-R-Y-H-H-R)

Referring to FIGS. 2a and 2b, structures of the synthetic peptides BFP 1 and BFP 2 are shown on the display terminals as reproduced by a commercially available program. As shown, the peptide sequences of FIGS. 1a and 1b are of alpha-helix structures.

An MTT assay for cytotoxicity shows that neither BFP 1 nor BFP 2 are toxic to cells within a range of used concentrations, as shown in FIGS. 3a and 3b.

A better understanding of the present invention may be obtained through the following examples which are set forth to illustrate, but are not to be construed as limiting the present invention.

EXPERIMENTAL EXAMPLE 1

The following experiments were conducted to assay BFP 1 and BFP 2 for activity related to the differentiation of osteoblasts.

1. Preparation of Osteoblasts and Osteogenic Differentiation Medium

Mesenchymal stem cells (cloned from Balb/c mouse bone marrow stromal cells) were seeded at a density of $1\times10^4$ cells/well in DMEM supplemented with 10% FBS on plates, followed by incubation for 3 days at 37° C. in a 5% $CO_2$ atmosphere to prepare osteoblasts.

An osteogenic differentiation medium (hereinafter referred to as "ODM") was prepared by supplementing DMEM with 50 µg/ml ascorbic acid, $10^{-8}$ M dexamethasone and 10 mM beta-glycerocellophosphate.

2. Assay for Mineralization

When the mesenchymal stem cells differentiate into osteoblasts, calcium is accumulated. Thus, the accumulation of calcium ions signals osteoblast differentiation and can be quantitatively detected through alizarin red S staining because Alizarin red S staining appears as gross and microscopic observation of osteoblasts differentiated from mesenchymal stem cells.

Therefore, cells treated with BFP 1 and/or BFP 2 in osteogenic differentiation media can be assayed for osteoblast differentiation by observing alizarin red S staining.

In more detail, mesenchymal stem cells were cultured for three days in an osteogenic differentiation medium and then for an additional two days in the presence of BFP 1 at a concentration of 0.1 µg/ml, 1 µg/ml and 2 µg/ml.

The same procedure was conducted for BFP 2.

Afterwards, the cells were fixed for one hour with ice-cold 70% ethanol and stained for 10 min with an alizarin red-s solution to observe calcium accumulation, that is, accumulation in terms of red color. The results are shown in FIGS. 4a and 4b.

Figure 4:
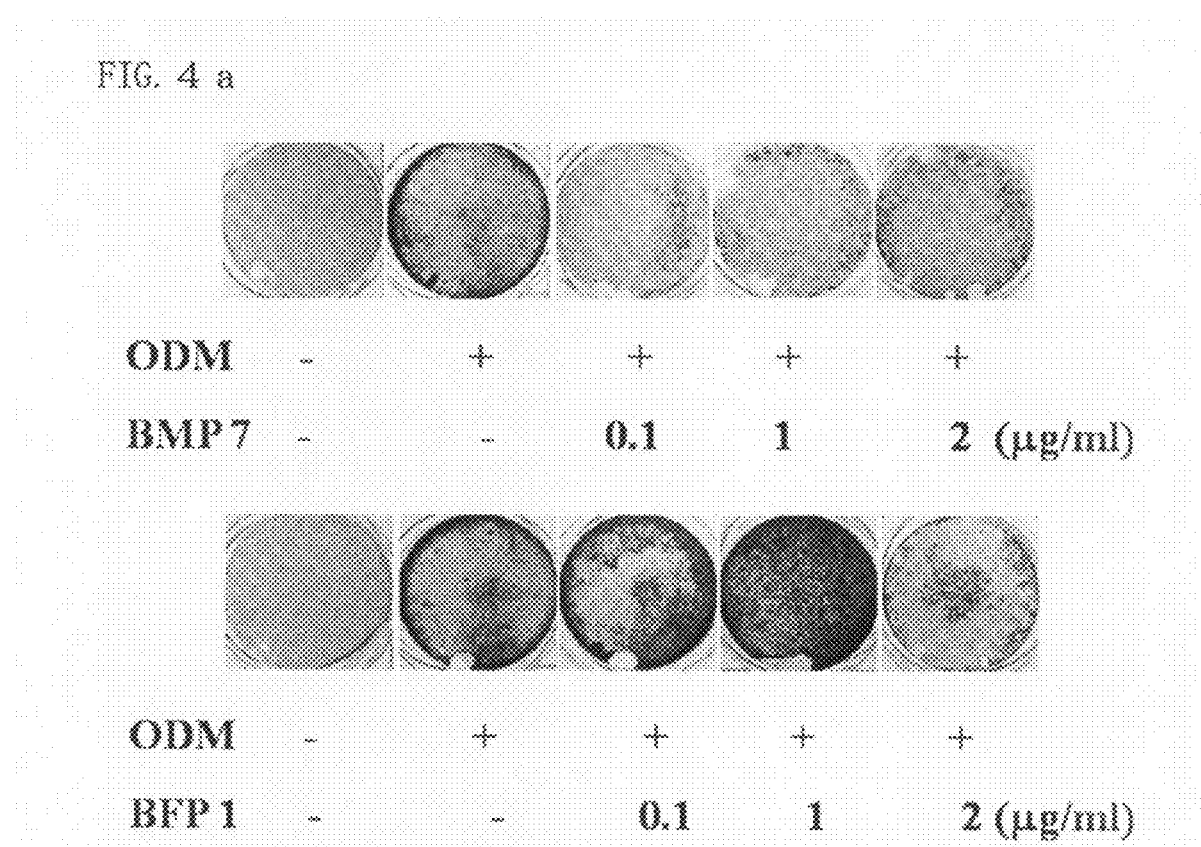
FIGS. 4a and 4b are photographs showing the mineralization visualized by alizarin red staining during osteoblast differentiation in the presence of BFP 1 and BFP 2.
Figure 4:
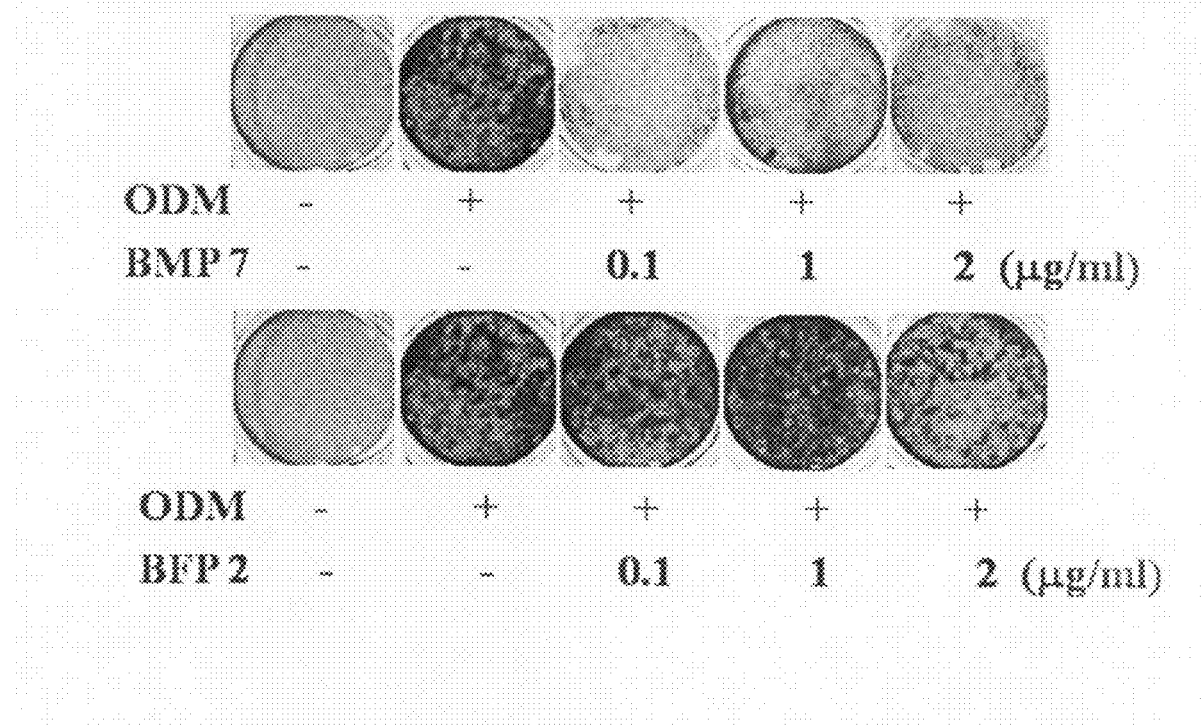

From the data of FIGS. 4a and 4b which show alizarin red-stained cells treated respectively with the BMP-7-derived, osteogenic synthetic peptides BFP 1 and BFP2, accounting for osteoblast differentiation in terms of mineralization, the most intense colors were observed in the cells treated with BFP 1 or BFP 2 at a concentration of 1 µg/ml. Also, more intense colors appeared in the cells treated with BFP 1 or BFP 2 than with those treated with BMP-7, indicating that BFP 1 or BFP 2 are more effective in inducing osteoblast differentiation than is BMP-7.

EXPERIMENTAL EXAMPLE 2

Figure 5A:
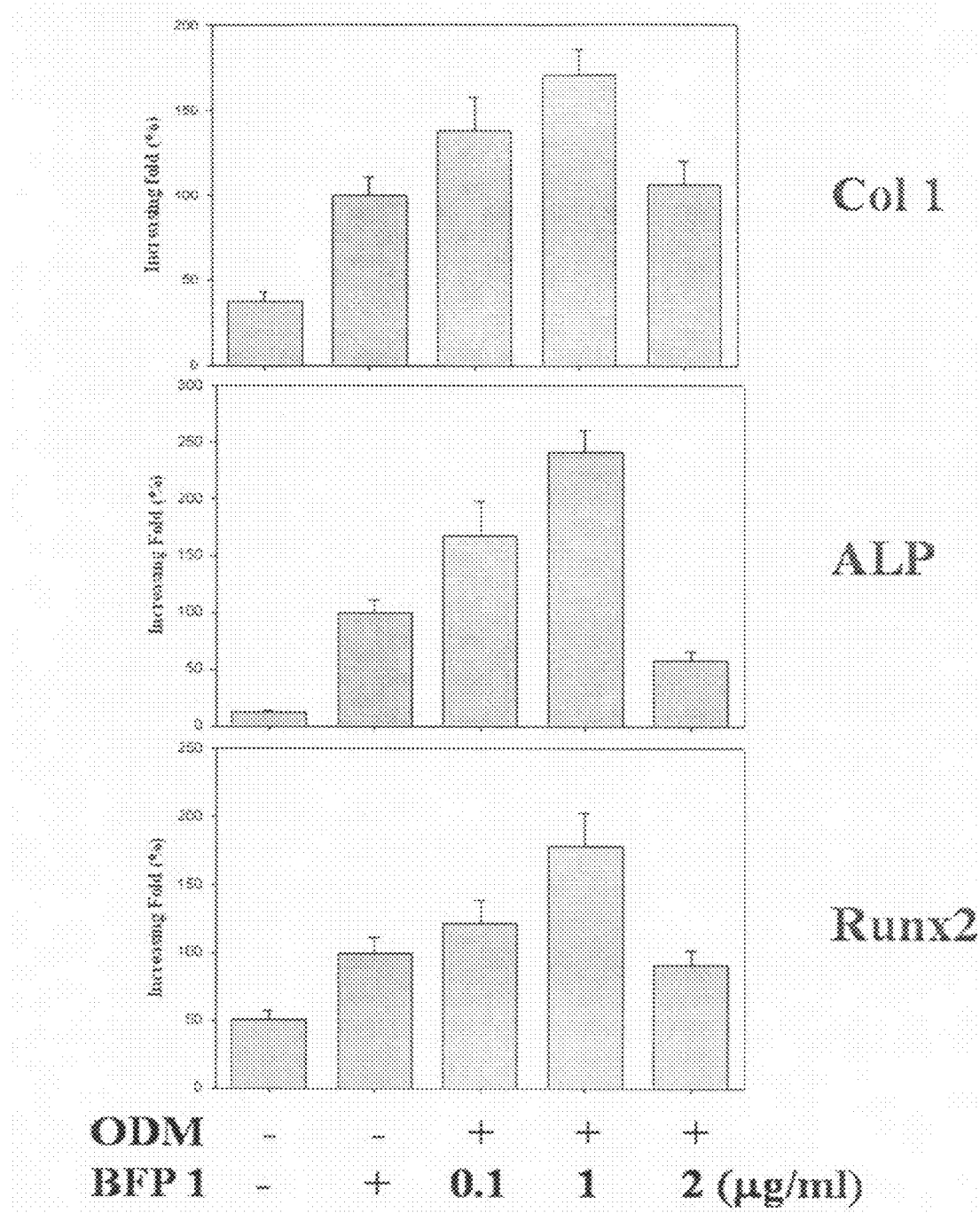
FIG. 5a is of histograms showing the effects of BFP 1 on the expression of osteoblast-specific genes; type-1 collagen, alkaline phosphatase (ALP) and Runx-2
Figure 5:
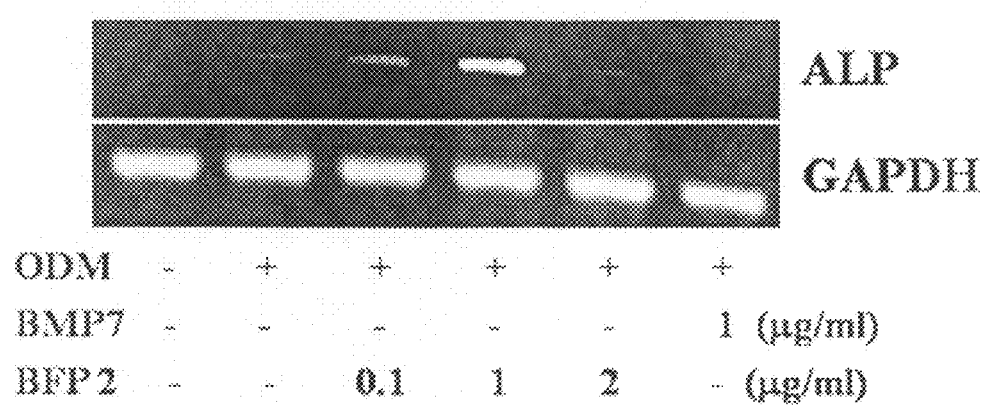
FIG. 5b is of histograms showing the effect of BFP 2 on the expression of osteoblast-specific alkaline phosphatase (ALP) gene.

An experiment was conducted to examine the effect of the osteogenic synthetic peptide BFP 1 on the expression of osteoblast specific genes, type 1 collagen, alkaline phosphatase and Runx-2 genes. The results are depicted in FIG. 5a.

When differentiation into osteoblasts starts, the genes specific for osteoblasts are expressed. The expression of these genes can be detected by real-time PCR. As a result, in the presence of BFP 1 at a concentration of 1 µg/ml, the expression level was measured to increase by 171% for type 1 collagen, by 241% for alkaline phosphatase and by 178% for Runx2, as expressed as percentages of that obtained in an osteogenic differentiation medium free of BFP 1.

As for BFP 2, its effect on the expression of the osteoblast-specific alkaline phosphatase gene was analyzed using reverse transcription PCR (RT-PCR). The results are given in FIG. 5b.

The expression level of alkaline phosphatase was observed to be the most intense in the presence of BFP 2 at a concentration of 1 µg/ml.

EXPERIMENTAL EXAMPLE 3

Figure 7A:
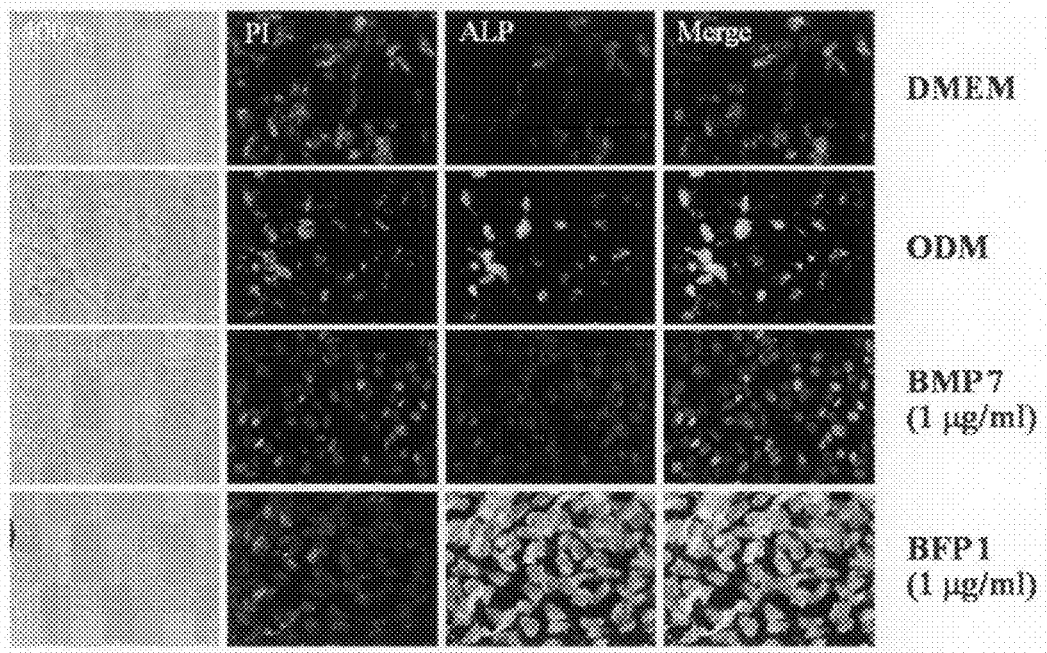
FIGS. 7a and 7b are of fluorescence microphotographs showing the expression of the osteoblast-specific alkaline phosphatase (ALP) gene in the presence of BFP 1 and BFP 2, respectively.
Figure 7B:
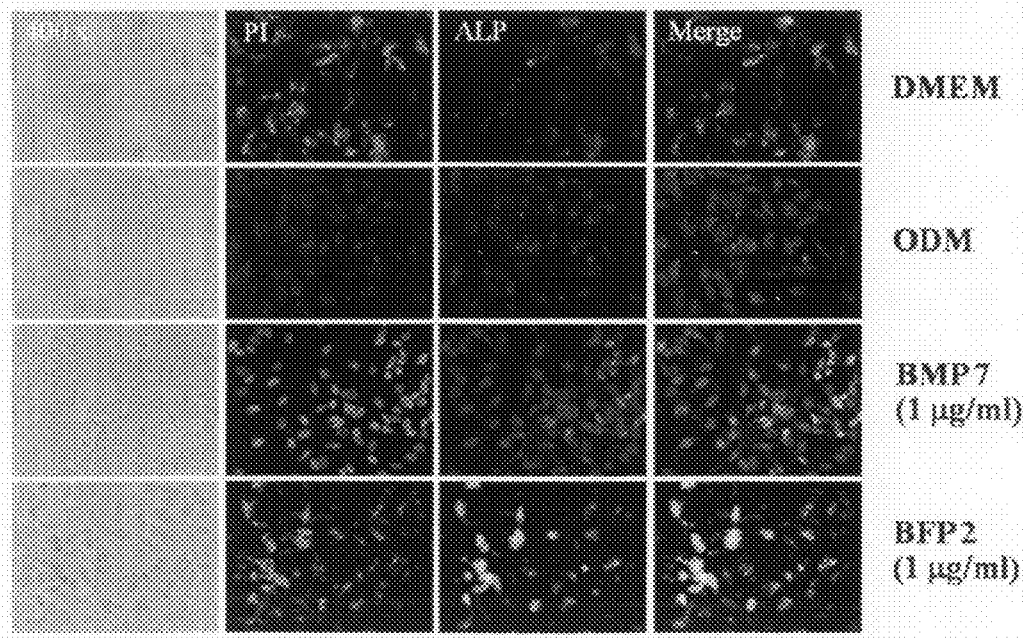
Figure 8:
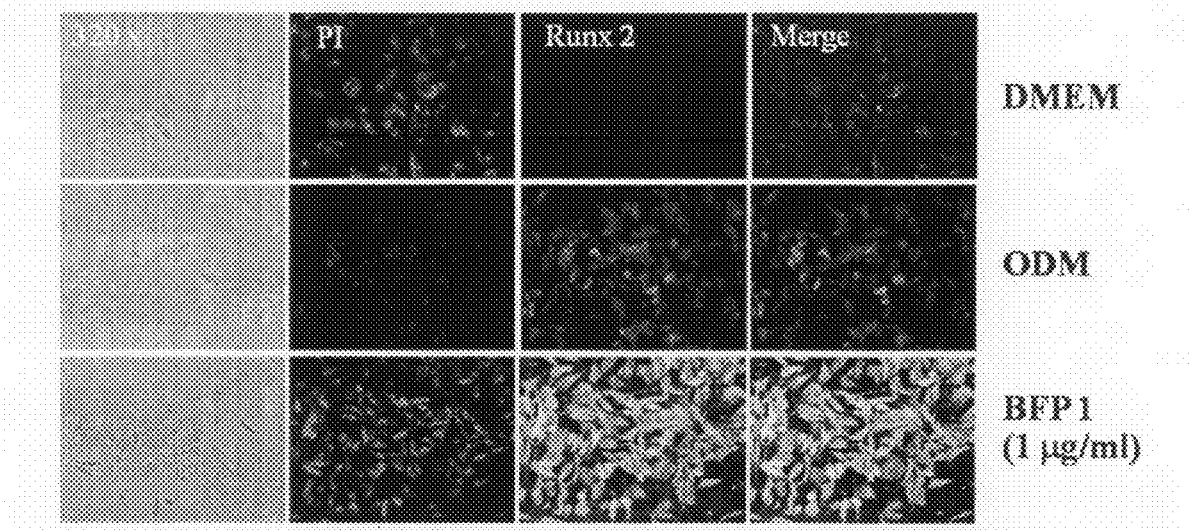
FIGS. 8a and 8b are of fluorescence microphotographs showing the expression of the osteoblast-specific Runx-2 gene in the presence of BFP 1 and BFP 2, respectively.
Figure 8:
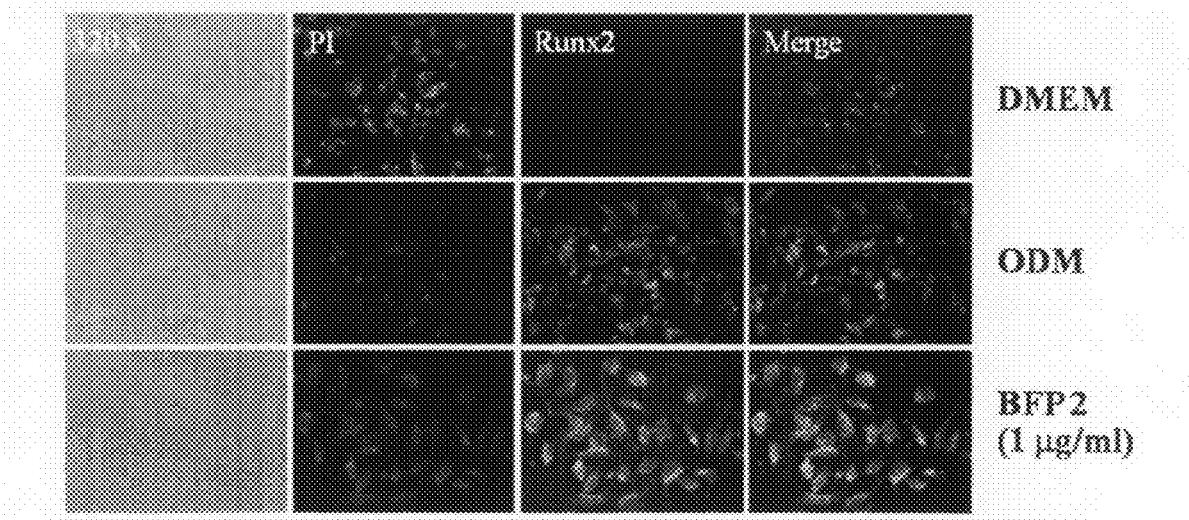

An examination was made of the effects of BFP 1 and BPF 2 on osteoblast differentiation. For this, the expression levels of osteoblast-specific genes, osteocalcin, alkaline phosphatase and Runx-2 were detected using fluorescent antibodies thereto and observed under a fluorescence microscope. The results are given in FIGS. 6 to 8, respectively.

In detail, differentiation into osteoblasts was accompanied by the expression of osteoblast-specific proteins which were then reacted with antibodies thereof. The antibodies bound to the proteins were observed under a fluorescence microscope. The fluorescence microscopy showed that osteocalcin, a bone matrix material secreted from osteoblasts whose higher levels are well correlated with an increase in the growth and differentiation of an osteoblast, was expressed at a higher level in an osteogenic differentiation medium (ODM) supplemented with 1 µg/ml of BFP 1 or BFP 2 than in an osteogenic differentiation alone or supplemented with BMP-7 as observed by the more intense green color (brighter portions in the drawings).

Figure 6A:
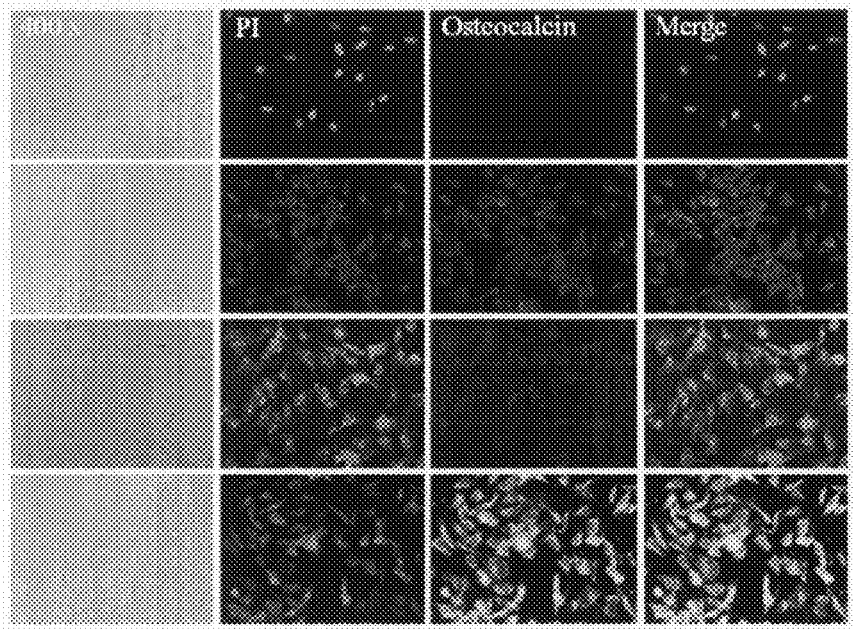
FIGS. 6a and 6b are of fluorescence microphotographs showing the expression of the osteoblast-specific osteocalcin gene in the presence of BFP 1 and BFP 2, respectively.
Figure 6B:
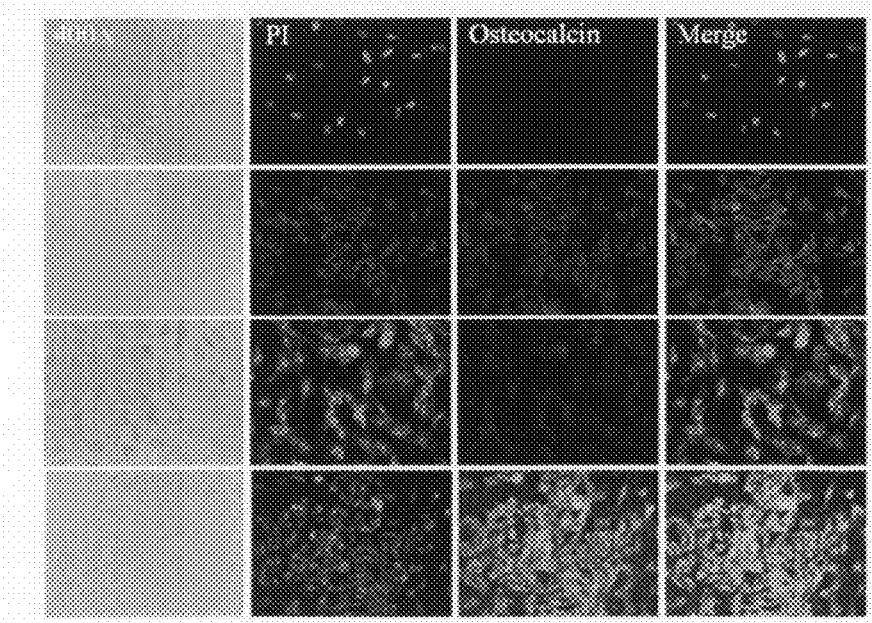

In FIGS. 6a and 6b, the PI panels are of stained nuclei of living cells, indicating living cells while the target protein osteocalcin appeared green from the cells due to the fluorescent antibodies thereof. The merge panels, resulting from overlapping the PI panels with the target protein panels, show the expression of the target protein from the same cells.

Expressed in a mid-phase of osteoblast differentiation, alkaline phosphatase serves as a biomarker for bone formation. Alkaline phosphatase was found to be expressed at higher levels in the presence of 1 µg/ml of BFP 1 or BFP 2, as well.

Runx-2, as a transcription factor of an osteoblast-specific protein, plays an important role in osteoblast differentiation. A higher expression level of Runx-2 was also detected in the presence of 1 µg/ml of BFP 1 or BFP 2.

EXPERIMENTAL EXAMPLE 4

Having various surface proteins, mesenchymal stem cells can differentiate into various cell types including osteoblasts, chondrocytes, adipocytes, myocytes, tendons, ligaments, neurons, and blood vessels. The effects of BFP 1 and BFP 2 on the differentiation of mesenchymal stem cells into osteoblasts were analyzed by FACS for the expression of osteoblast-specific surface proteins CD44, CD51, CD47 and CD45. The results are shown in FIGS. 9a and 9b.

With reference to FIG. 9a, the expression of the surface markers accounting for osteoblast differentiation was analyzed using FACS (gray arrows—ODM alone; black arrows—ODM+BFP 1). BFP 1 was observed to induce the expression of CD44, a surface marker for differentiation from mensenchymal stem cells to osteoblasts. Particularly in the presence of BFP 1 at a concentration of 1 µg/ml in an osteogenic differentiation medium, CD44 was expressed at a higher level. On the other hand, CD47 and CD51, both specific for osteoblasts, were observed to be expressed at higher levels in an ODM supplemented with BFP 1 than in an ODM alone.

With reference to FIG. 9b, the expression of the surface markers accounting for osteoblast differentiation was analyzed using FACS (gray arrows—ODM alone; black arrows—ODM+BFP 2). As shown in FIG. 9b, BFP 2 was observed to induce the expression of CD44, a surface marker for differentiation from mensenchymal stem cells to osteoblasts. Particularly in the presence of BFP 2 at a concentration of 1 µg/ml in an osteogenic differentiation medium, CD44 was expressed at a higher level.

In addition, CD51, specific for osteoblasts, was observed to be expressed at higher levels in an ODM supplemented with BFP 1 than in an ODM alone.

On the other hand, CD45, a surface factor located in hematopoietic cells, was used to show that the cells used in this experiment were not derived from a hematopoietic line. As seen in FIGS. 9a and 9b, no CD45 was expressed, indicating that the cells used in this experiment were not derived from hematopoietic stem cells.

EXPERIMENTAL EXAMPLE 5

The effects of BFP 1 and BFP 2 on the expression of the surface marker CD44 were observed under a fluorescence microscope and the results are given in FIGS. 10a and 10b.

During differentiation, the cells were stained with DAPI, a fluorescent stain that easily binds to the DNA of living cells, and with a PE(phycoerythrin)-conjugated-CD44 antibody.

The nuclei appeared blue while CD44 was stained red under fluorescence microscopy. When these stained images were merged, it was observed that CD44 was expressed on the DAPI-stained cells. Higher levels of CD44 were detected when an osteogenic differentiation medium was used in combination with BFP 1 or BFP 2 than when used alone. At the same concentrations, BMP-7 produced less intense staining in the cells than did BFP 1 or BFP 2 under a fluorescence microscope.

EXPERIMENTAL 6

When osteoblast differentiation was permitted in the presence of BFP 1 or BFP 2, the concentrations of osteoblast-specific alkaline phosphatase (ALP) and calcium were measured using a commercially available diagnostic kit. The results are depicted in FIGS. 11a and 11b.

Figure 11B:
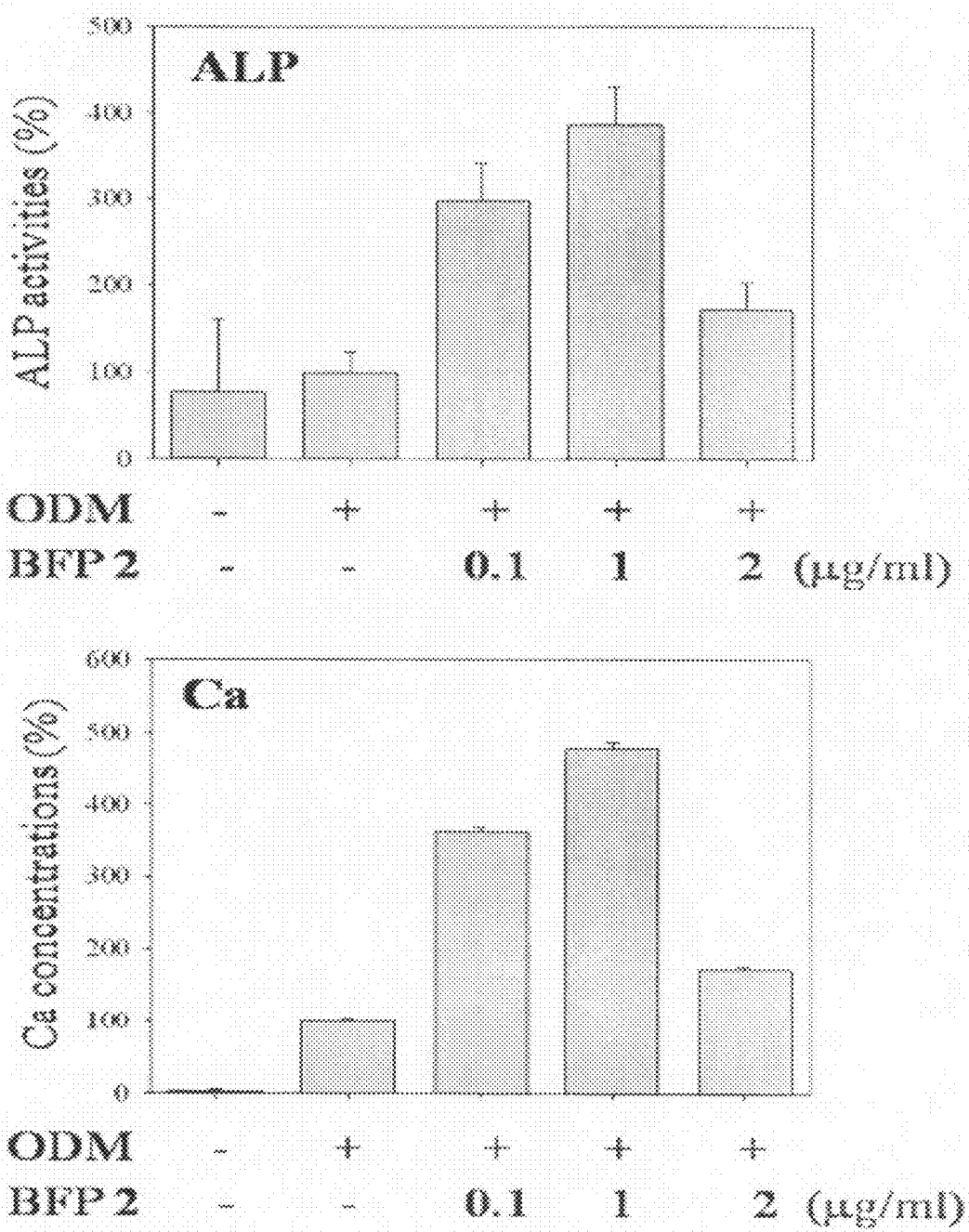

Significant increases in the levels of both ALP and calcium were observed in the presence of BFP 1 or BFP 2 at a concentration of 1 µg/ml, as seen in FIGS. 11a and 11b.

EXPERIMENTAL 7

Cells were treated with FITC-conjugated-BFP 1 before observation under a fluorescence microscope in order to examine how the synthetic BFP 1 of the present invention acts on cells. The results are shown in FIG. 12.

Figure 12:
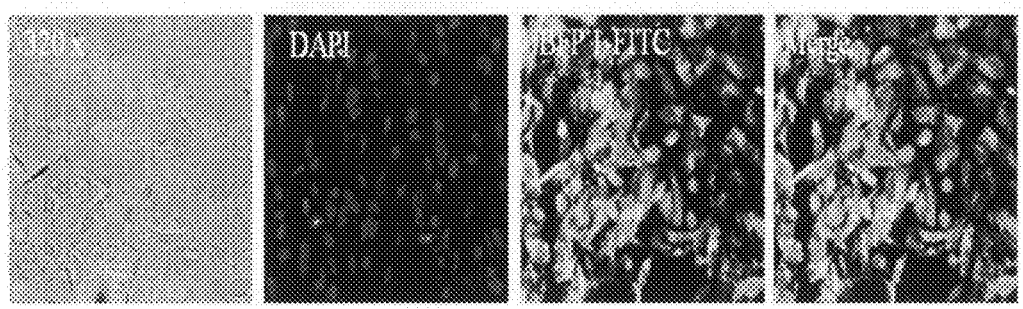
FIG. 12 is of fluorescence microphotographs taken of cells treated with FITC-conjugated BFP 1.

As seen in FIG. 12, FITC-conjugated BFP 1 entered cells and acted within cells.

EXPERIMENTAL EXAMPLE 8

Figure 13A:
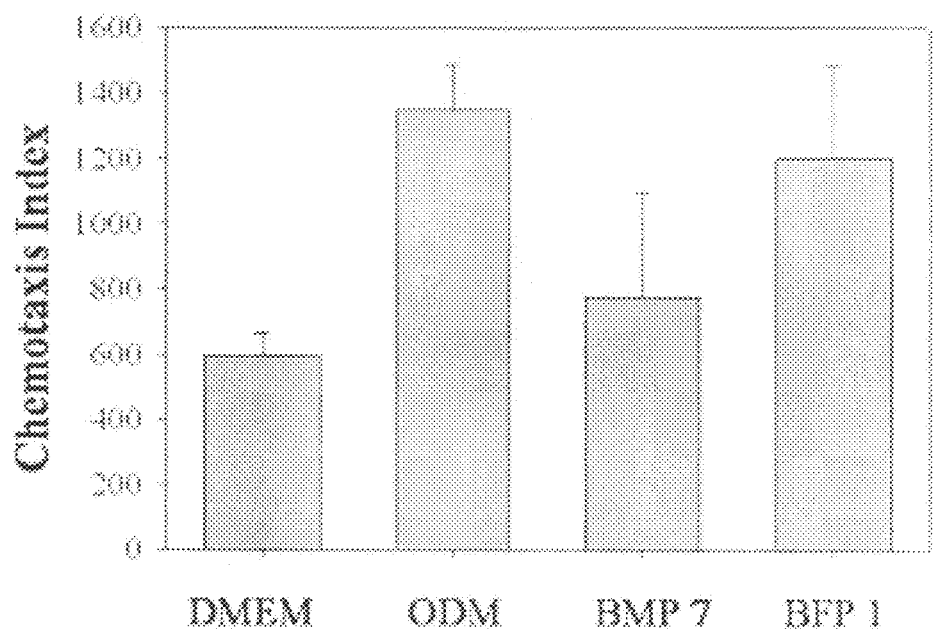
FIGS. 13a and 13b are of histograms showing the migration of cells to BFP 1 and BFP 2, respectively, via a chemotaxis assay during differentiation from mesenchymal stem cells to osteoblasts.
Figure 13B:
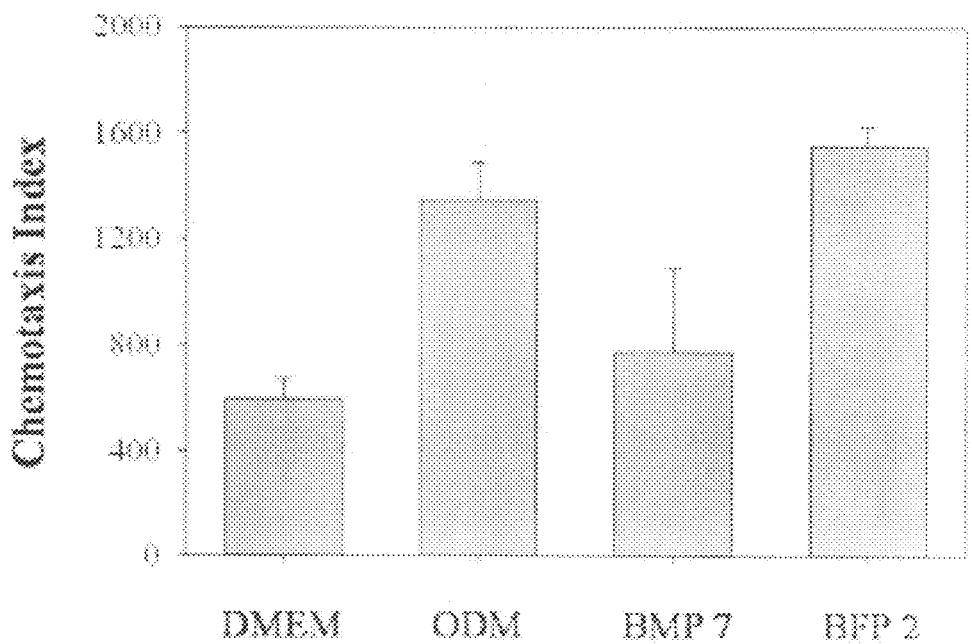

While differentiating into osteoblasts, BFP 1 and BFP 2 were added to mesenchymal stem cells to examine chemotaxis and cell migration. The results are shown in FIGS. 13a and 13b.

For this, mesenchymal stem cells were incubated in osteogenic differentiation media supplemented with BMP-7, BFP 1 or BFP 2. As seen in FIGS. 13a and 13b, more cells were observed to migrate in the presence of BFP 1 or BFP 2 than in the presence of BMP-7, indicating that BFP 1 or BFP 2 according to the present invention can induce osteoblasts to rapidly migrate to lesions of bone diseases such as bone defects.

EXPERIMENTAL EXAMPLE 9

To examine whether BFP 1 and BFP 2 can promote osteogenesis in vivo, mice were employed (n=6). In this context, first, mesenchymal stem cells were treated twice with ODM for 3 days in order to induce osteoblast differentiation. Upon the second treatment, BMP-7, BFP 1 or BFP 2 was added to the ODM. After incubation for 24 hrs in the second ODM, cells were harvested and counted. A predetermined number of the cells were implanted into the back of mice with collagen serving as a support. Four and eight weeks after the implantation, pictures were taken of the mice with X-ray in order to examine bone formation therein. The results are shown in FIGS. 14a and 14b. Particularly, tissues were excised at Week 8 and decalcified, followed by staining with hematoxylin & eosin to examine the morphology thereof. The photographs are given in FIGS. 15a and 15b.

As seen in the X-ray photographs of FIGS. 14a and 14b, bone appeared at the site treated with BFP 1 or BFP 2 on Week 4. The photographs taken on Week 8 show greater bone formation at the sites treated with BFP 1 or BFP 2 than with BMP-7.

Figure 15A:
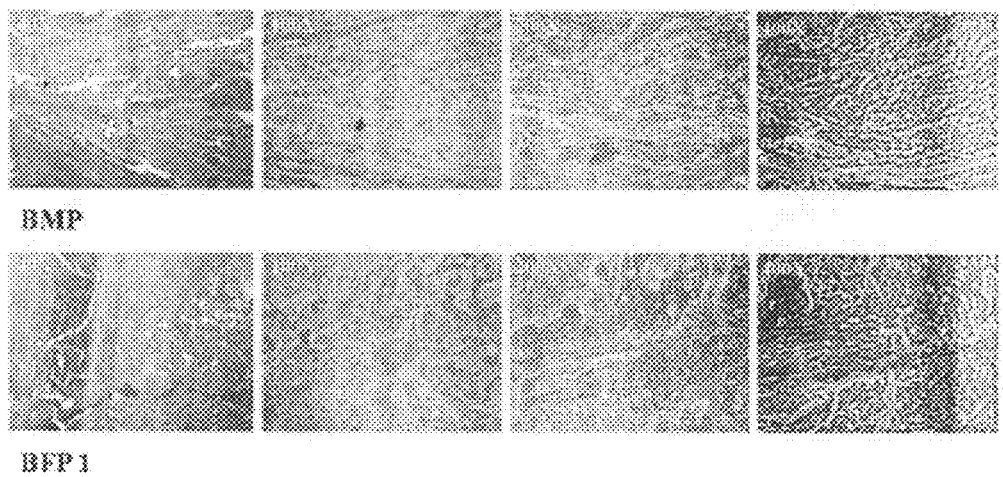
FIGS. 15a and 15b are histochemistry photographs of tissues taken from mice on Week 8 after implantation with BFP 1- or BFP 2-treated cells, visualized by hematoxylin & eosin staining, showing the effect of BFP 1 and BFP 2 on bone formation.
Figure 15B:
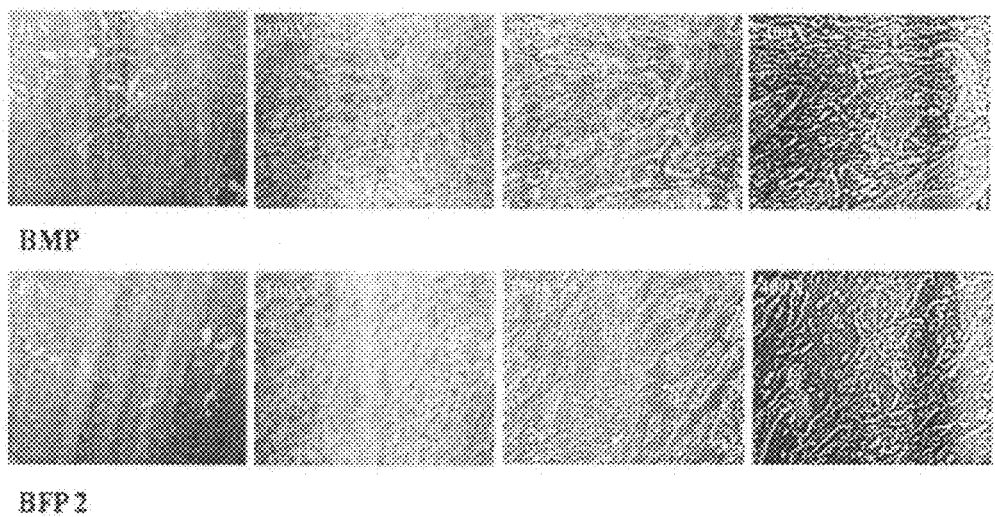

In addition, as shown in FIGS. 15a and 15b, the osteogenic peptides BFP 1 and BFP 2 in accordance with the present invention induced bone formation like as BMP7 control.

From the data, it is apparently understood that the osteogenic synthetic peptides of the present invention, BFP1 and BFP2, play a more important role in osteoblast differentiation and bone formation than does BMP-7, known as an osteogenesis promoter, and can induce osteogenesis to the same or a higher extent and over a broader range than can BMP-7.

Therefore, the present invention provides a pharmaceutical composition comprising the osteogenic synthetic peptide of the present invention or a non-toxic salt thereof in combination with a pharmaceutically or veterinarilly acceptable liquid or solid carrier. As long as it is known in the art, any pharmaceutically or veterinarilly acceptable liquid or solid carrier can be used in the present invention without limitation. Thus, a detailed description is not given of the carrier.

Particularly, the data of Experimental Example 9 shows the in vivo bone formation effect of BFP 1 and BFP 2, suggesting that when applied to the bone marrow affected with osteoporosis and/or osteoarthritis, the osteogenic synthetic peptides, BFP 1 and BFP 2, or a pharmaceutical composition comprising the same can promote the differentiation of the bone marrow into osteoblasts, leading to bone formation. Therefore, the pharmaceutical composition of the present invention may be used as a therapeutic for osteoporosis and/or osteoarthritis.

Likewise, when applied to bone defective sites, the pharmaceutical composition comprising the osteogenic synthetic peptide, BFP 1 or BFP 2, or a non-toxic salt thereof can effectively conduct bone restoration through bone formation.

Although specified as examples, it is apparent to those in the art that when added to osteogenic differentiation media, the osteogenic synthetic peptide according to the present invention, BFP 1 or BFP 2, allows the user to easily control the experiments with osteoblasts.

Being able to promote osteoblast differentiation and thus bone formation, as described hitherto, the osteogenic synthetic peptides of the present invention find useful applications in various fields related with osteoblast differentiation or bone formation In addition, the pharmaceutical composition comprising the osteogenic synthetic peptides in accordance with the present invention is useful in the treatment of osteoporosis, osteoarthritis and/or bone defects with few side effects compared to conventional pharmaceutical compositions and is effective in promoting bone formation through the promotion of osteoblast differentiation in addition to being economically favorable thanks to the low production cost thereof.

Further, the medium composition containing the osteogenic synthetic peptide of the present invention allows the user to control the rate of osteoblast differentiation thereby enabling the set up of a variety of experimental conditions.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An isolated peptide consisting of the amino acid sequence of SEQ ID NO. 1.

2. A pharmaceutical composition comprising the peptide of claim 1 or a pharmaceutically acceptable salt thereof alone, or in combination with a pharmaceutically or veterinarilly acceptable liquid or solid vehicle.

3. The pharmaceutical composition of claim 2, wherein an effective amount of the peptide is from 0.1 to 2 μg/ml.

* * * * *